United States Patent [19]

Seto et al.

[11] Patent Number: 4,843,076
[45] Date of Patent: Jun. 27, 1989

[54] DIHYDROPYRIDINE-5-PHOSPHONIC ACID CYCLIC ESTER

[75] Inventors: Kiyotomo Seto; Ryozo Sakoda; Hiroo Matsumoto; Yoshimasa Kamikawaji, all of Funabashi; Sakuya Tanaka, Shiraoka, all of Japan

[73] Assignee: Nissan Chemical Industries Ltd., Tokyo, Japan

[21] Appl. No.: 77,220

[22] Filed: Jul. 24, 1987

Related U.S. Application Data

[63] Continuation-in-part of Ser. No. 792,981, Oct. 30, 1985, and Ser. No. 851,158, Apr. 14, 1986, said Ser. No. 792,981, is a continuation-in-part of Ser. No. 654,473, Sep. 26, 1984, Pat. No. 4,576,934.

[30] Foreign Application Priority Data

Sep. 10, 1986 [JP] Japan .................................. 61-213412

[51] Int. Cl.⁴ .................... C07D 401/12; A61K 31/44
[52] U.S. Cl. ..................................... 514/252; 544/337
[58] Field of Search .................. 544/337; 514/252; 546/321

[56] References Cited

U.S. PATENT DOCUMENTS

| 4,380,547 | 4/1983 | Materne | 546/270 |
| 4,510,310 | 4/1985 | Wehinger et al. | 546/321 |
| 4,576,934 | 3/1986 | Seto et al. | 546/21 |

OTHER PUBLICATIONS

Hackh's Chemical Dictionary, 4th Edition, p. 574.

*Primary Examiner*—Jane T. Fan
*Attorney, Agent, or Firm*—Oblon, Spivak, McClelland, Maier & Neustadt

[57] ABSTRACT

An optical isomer of a compound having the formula:

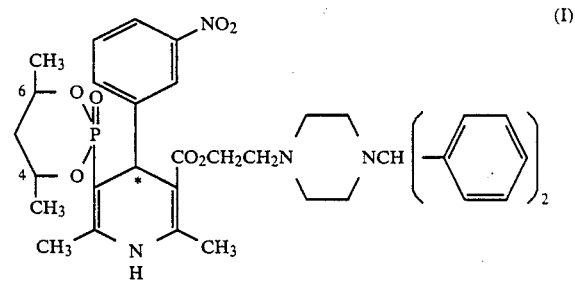

wherein the two methyl groups at 4- and 6-positions of the dioxaphosphorinane ring assume trans configurations to each other, which has a levo-rotatory angle of optical rotation attributable to the asymmetric carbon atom at 4-position of the dihydropyridine ring, and a pharmaceutically acceptable salt thereof.

5 Claims, No Drawings

DIHYDROPYRIDINE-5-PHOSPHONIC ACID CYCLIC ESTER

RELATED APPLICATIONS

This application is a continuation in part of application Ser. Nos. 792,981 and 851,158, filed Oct. 30, 1985 and Apr. 14, 1986, respectively. U.S. Ser. No. 792,981 is a continuation-in-part of U.S. Ser. No. 654,473, filed Sept. 26, 1984, now issued as U.S. Pat. No. 4,576,934 on Mar. 18, 1986.

FIELD OF THE INVENTION

The present invention relates to optically active 1,4-dihydropyridine-5-phosphonic acid derivatives having vasodilation activities and pharmaceutically acceptable salts thereof.

DISCUSSION OF BACKGROUND

A compound having the formula:

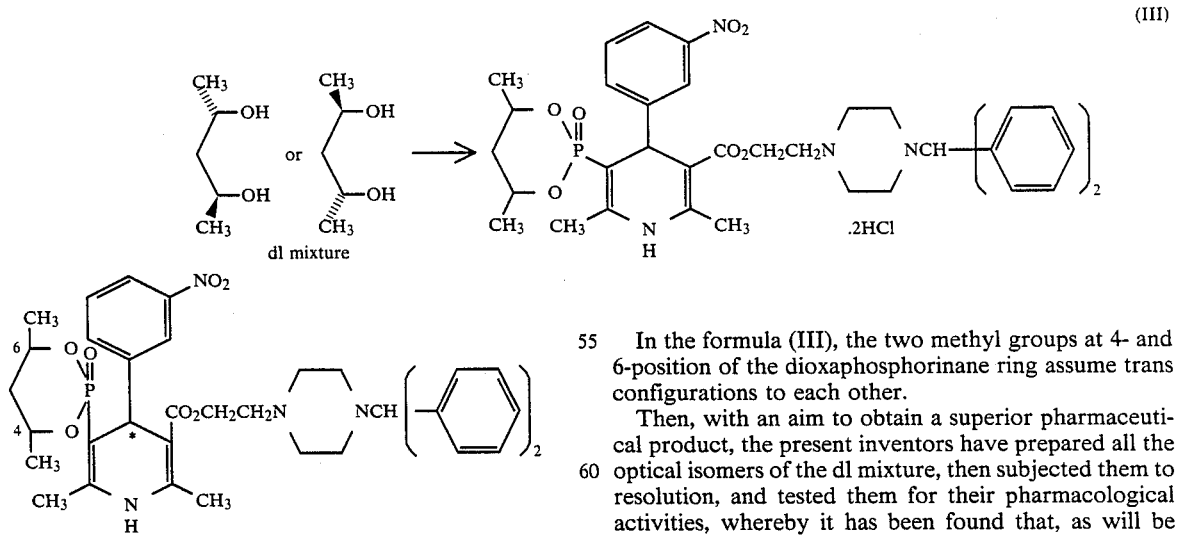

(I)

(hereinafter referred to as Compound (I)) is disclosed in U.S. Pat. No. 4,576,934 (hereinafter referred to as Reference (a)).

Compound (I) has excellent characteristics such that it gradually reduces the blood pressure without substantially affecting the heart rate, and yet such action lasts for a long period of time. [Lecture No. A-9, delivered on Oct. 13, 1985 at the 73rd Meeting of Kanto Division of Nippon Pharmacological Association (hereinafter referred to as Reference (b))]

Compound (I) has three asymmetric carbon atoms, and it should have optical and stereo isomers. However, the above-mentioned References (a) and (b) disclose nothing on such isomers.

SUMMARY OF THE INVENTION

As Compound (I) has three asymmetric carbon atoms, eight optical isomers are expected to exist. The present inventors have synthesized two isomers among them by using the meso isomer (the R,S isomer) and the dl mixture (a mixture of the R,R isomer and the S,S isomer) of 2,4-pentanediol as the starting material, and have tested them for their pharmacological activities, whereby it has been found that only the isomer of the formula (II) prepared from the meso isomer has a strong negative activity for cardiac muscle.

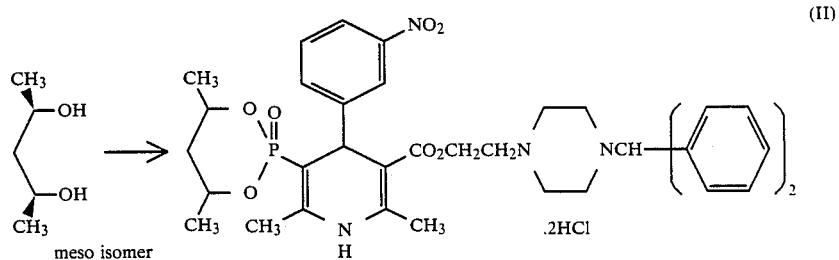

In the above formula (II), the two methyl groups at 4- and 6-positions of the dioxaphosphorinane ring assume cis configurations to each other.

In the formula (III), the two methyl groups at 4- and 6-position of the dioxaphosphorinane ring assume trans configurations to each other.

Then, with an aim to obtain a superior pharmaceutical product, the present inventors have prepared all the optical isomers of the dl mixture, then subjected them to resolution, and tested them for their pharmacological activities, whereby it has been found that, as will be apparent from the pharmacological test results given hereinafter, levo-rotatory isomers of the formulas (V) and (VIII) exhibit remarkably superior effects as compared with dextro-rotatory isomers of the formulas (VI) and (IX). The present invention has been accomplished on the basis of this discovery.

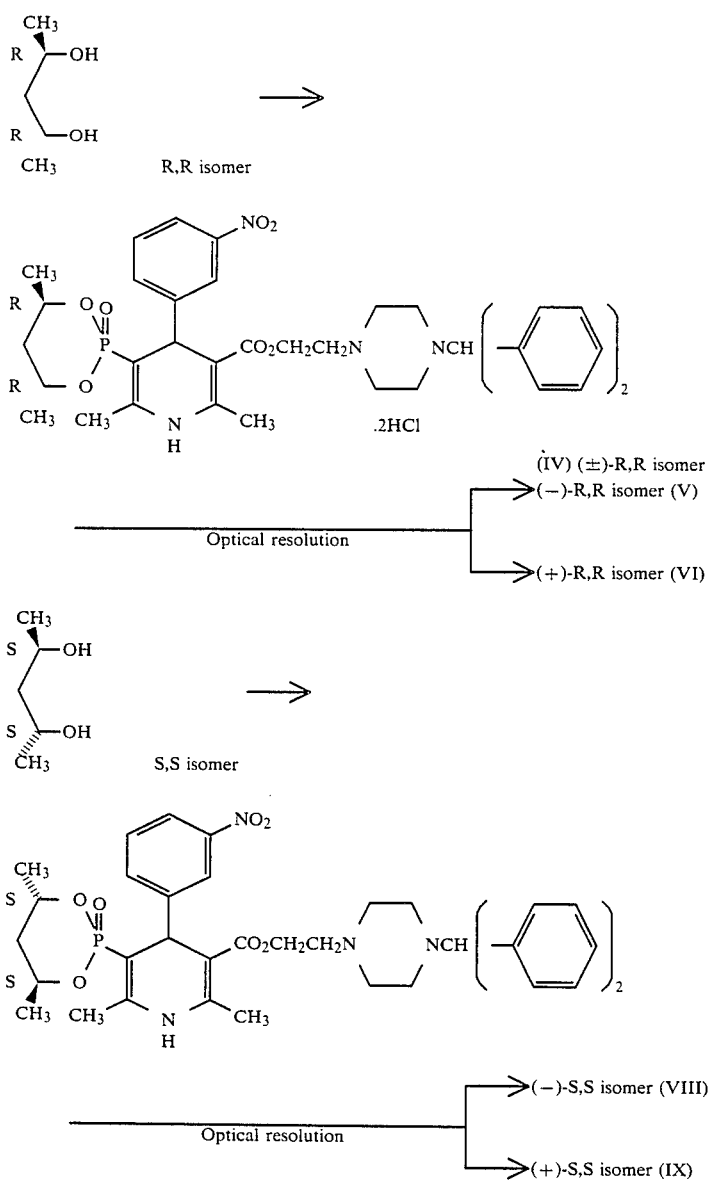

(IV) (±)-R,R isomer
→ (−)-R,R isomer (V)
Optical resolution
→ (+)-R,R isomer (VI)

→ (−)-S,S isomer (VIII)
Optical resolution
→ (+)-S,S isomer (IX)

Namely, the present invention provides an optical isomer of a compound having the formula:

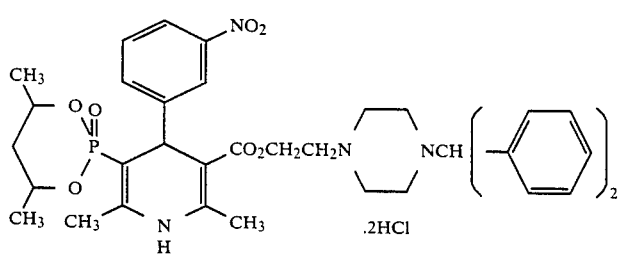

(I)

wherein the two methyl groups at 4- and 6-positions of the dioxaphosphorinane ring assume trans configurations to each other, which has a levo-rotatory angle of optical rotation attributable to the asymmetric carbon atom at 4-position of the dihydropyridine ring, and a pharmaceutically acceptable salt thereof.

DETAILED DESCRIPTION OF THE PREFERRED EMBODIMENTS

Now, the synthesis of the compound of the present invention will be described.

The process steps for the synthesis of the compound of the present invention are as follows (in each of the following steps, a R,R form product is obtained from a R,R form starting material, and a S,S form product is obtained from a S,S form starting material.)

Then, the respective hydochlorides are dissolved in ethanol under heating, and cooled, whereby a (−)-

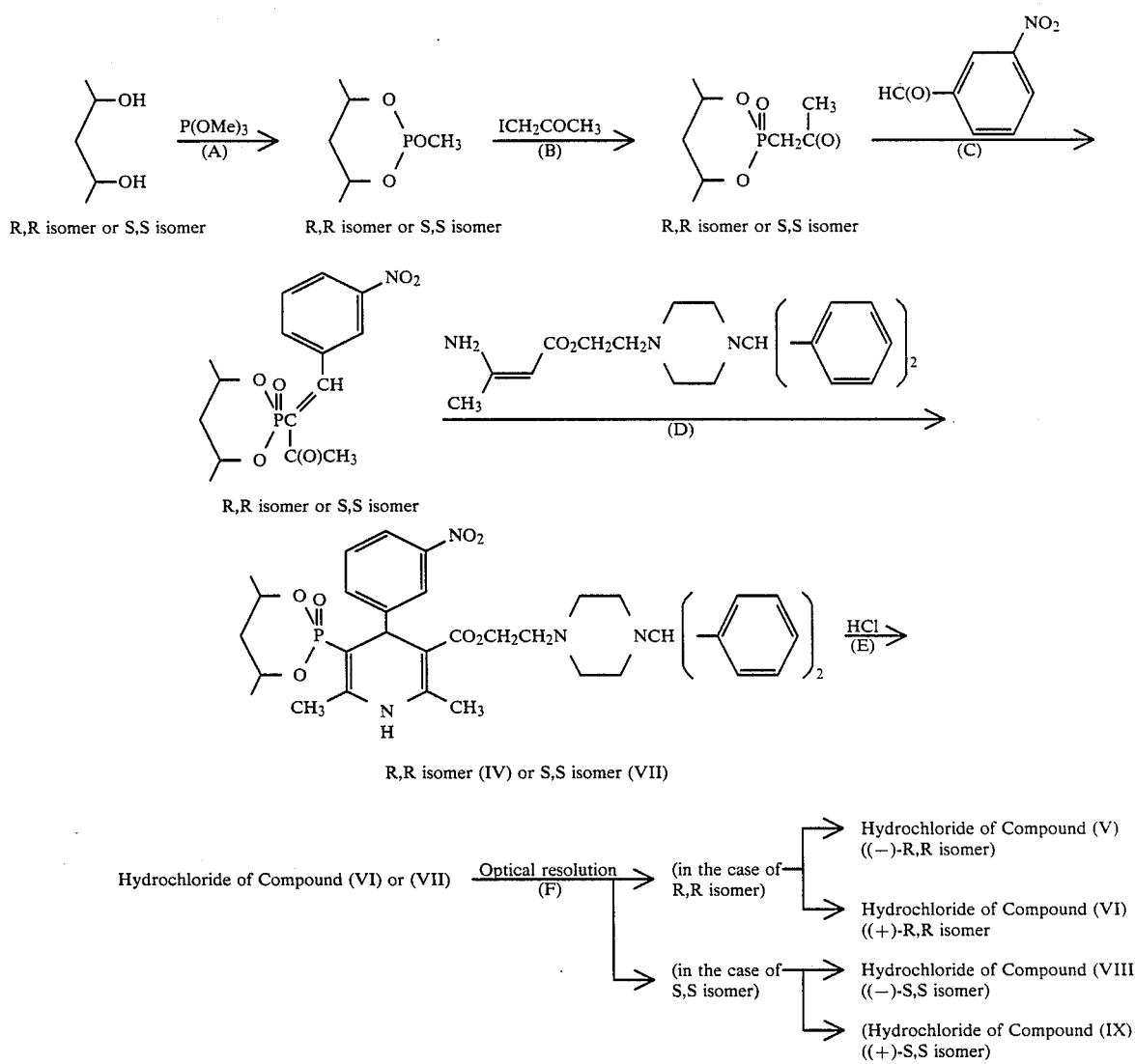

Above Steps (A), (B) and (C) are conducted by conventional methods in accordance with Reference Examples given hereinafter. The product obtained in Step (C) may be used for the next Step (D) without purification or isolation.

In Step (D), an inert solvent is employed. The inert solvent may be an alcohol solvent such as methanol, ethanol, propanol or isopropanol, an ether solvent such as 1,2-dimethoxyethane or THF, an aromatic hydrocarbon solvent such as benzene, toluene or xylene, a nitrile solvent such as acetonitrile or benzonitrile, an amide solvent such as DAM, DMF or N-methylpyrrolidone, a sulfoxide solvent such as DMSO or sulfolane, an ester solvent such as ethyl acetate or butyrolactone, or pyridine.

The reaction is conducted at a temperature within a range of from room temperature to 200° C., preferably from 60° to 140° C., for from 1 to 100 hours, preferably from 5 to 20 hours.

Compound (IV) or (VII) obtained in Step (B) is reacted with hydrochloric acid to obtain a hydrochloride of Compound (IV) or (VII) (Step (E)).

product precipitates from the ethanol solution of the R,R isomer, and a (+)-product precipitates from the ethanol solution of the S,S isomer. The precipitates are collected from the respective ethanol solutions, and, if necessary, recrystallized from ethanol to obtain highly pure (−)-R,R isomer and (+)-S,S isomer, respectively (Step (F)).

After the collection of the precipitates from the respective ethanol solutions, the respective ethanol filtrates are subjected to distillation under reduced pressure to remove the solvent to dryness, and the dried residue is recrystallized from acetone to obtain a (+)-R,R isomer from the acetone solution of the R,R isomer. Whereas, from the acetone solution of the S,S isomer, a (−)-S,S isomer is obtained. For further purification of these products, the recrystallized products from acetone are dissolved in ethanol, the solvent is evaporated under reduced pressure to dryness, and the dried product is recrystallized from acetone.

The pharmaceutically acceptable salt is meant for a monoacid salt or diacid salt with a pharmacologically inactive acid. For example, it may be a hydrochloride, a sulfate, a nitrate, a lactate or a succinate.

Such a salt may be obtained by neutralizing the hydrochloride obtained in the above described method, and then adding the corresponding acid.

As will be apparent from the results of the antihypertensive tests given hereinafter, the compounds of the present invention have vasodilator activities, and thus useful for treating diseases of circulatory organs of mammals, such as angina pectoris, disturbance of cerebral circulation or hypertension.

Thus, the present invention provides a vasodilator composition comprising an effective amount of the optical isomer of the present invention or its pharmaceutically acceptable salt, and a pharmaceutically acceptable diluent or carrier. Such a composition may also be formulated into a veterinary composition by combining the compound of the present invention with a veterinarily acceptable diluent or carrier.

Such compositions may be used in the form suitable for oral administration, e.g. tablets or capsules, in the form suitable for transdermal administration, e.g. ointments or plasters, in the form suitable for inhalation, e.g. aerosols or solutions suitable for spraying, in the form suitable for injection administration, e.g. a sterilized aqueous solution, or in the form of a suppository suitable for use in anus, vagina or rectum.

The composition of the present invention usually contains the compound of the present invention in an amount of from about 0.1 to about 99.5% by weight, preferably from about 0.5 to about 95% by weight, based on the total weight of the composition.

The compound of the present invention or the composition of the present invention may be used in combination with other pharmaceutically or veterinarily active compounds. Further, the composition of the present invention may contain a plurality of the compounds of the present invention.

The daily dose of the compound of the present invention may be varied depending upon the type and the condition of the disease to be cured and the type of the patient (the age, sex, sensitivity, etc.). In the case of the intravenous administration, the daily dose is usually from 0.0001 to 10 mg, preferably from 0.0005 to 1 mg, of the active ingredient per 1 kg of the body weight. Likewise, in the case of the oral or transdermal administration, the daily dose is usually from 0.001 to 100 mg of the active ingredient per 1 kg of the body weight. Further, the daily dose in the case of the administration in the form of a suppository to e.g. a vagina or rectum, is usually from 0.001 to 200 mg, preferably from 0.005 to 100 mg, of the active ingredient per 1 kg of the body weight. The content of the active ingredient in an aerosol, is usually from 0.1 to 10% by weight, preferably from 0.1 to 2% by weight. Such a daily dose may be divided for administration twice or more times per day.

The above-mentioned composition containing the compound of the present invention may be prepared by a conventional method, and a conventional excipient may be incorporated therein.

Now, the present invention will be described in further detail with reference to Test Examples, Reference Examples, Working Examples and Formulation Examples. However, it should be understood that the present invention is by no means restricted to such specific Examples. In the following formulas, Ph means a phenyl group.

TEST EXAMPLE 1: Calcium antagonistic effects 10 mm in situ length of taenia caecum of guinea pig was suspended at a tension of 1 g in a 20 ml organ bath filled with a physiological salt solution (NaCl: 135 mM, KCl: 5 mM etc.).

This solution was bubbled with a gas mixture of 95% $O_2$-5% $CO_2$ and kept at 37° C. Then, the preparation was depolarized by a $K^+$ rich solution (NaCl: 40 mM, KCl: 100 mM). After 10-20 minutes equilibration period, 10 mM of $CaCl_2$ was added to the bathing solution. The contraction was produced, and then the test compound applied cumulatively. The relaxation produced was expressed as percentage of the maximum relaxation produced by $10^{-4}$M papaverine, and the concentration of the compound producing 50% relaxation, i.e. $ID_{50}$ (M), was calculated. The values of $pID_{50}$ ($pID_{50} = -\log [ID_{50}]$) are summarized in Table 1.

TEST EXAMPLE 2: Antihypertensive effects (Venous injection)

The antihypertensive effects of compounds of the present invention were tested by using spontaneously hypertenisve rats (SHR) anesthetized with urethane-α-chloralose. This test was conducted with a group of 3 to 5 SHR by measuring the blood pressure at the common carotid artery of each rat. Each test compound was dissolved in 3% tween 80-physiological salt solution, and injected into the femoral vein. From the relation between the dose and the maximum pressure drop, $ED_{30}$ (mg/kg) i.e. a dose required for 30% pressure drop, was obtained. The results are shown in Table 1.

TEST EXAMPLE 3: Antihypertensive effects (Oral administration)

A compound of the present invention was dissolved in a solvent of PEG:$H_2O$=3:1 and orally administered to a group of 4 SHR at a dose of 15 mg/kg. The blood pressure was measured by a tail-cuff method (by using KN-210-1, manufactured by Natsume Seisakusho).

The results were represented by the pressure drop (%) relative to the blood pressure prior to the administration, and are given in Table 1.

| Type of isomer | $pID_{50}$ | $ED_{30}$ (mg/kg) | mmHg(%) | | |
|---|---|---|---|---|---|
| | | | 2 hrs. | 4 hrs. | 6 hrs. |
| (V) (−)-R,R | 8.02 | 0.023 | 22 | 23 | 30 |
| (VI) (+)-R,R | 7.12 | 0.557 | 2 | −1 | — |
| (VIII) (−)-S,S | 7.94 | 0.048 | 22 | 27 | 1 |
| (IX) (+)-S,S | <6 | 1.659 | 0 | 4 | — |

TEST EXAMPLE 4: Toxicity test

The test compound was suspended in a 0.5% MC aqueous solution to obtain a 1 w/w% suspension, which was orally administered to three ddY male mice of 4 weeks old. The mice were observed for 7 days. No mice died even at a dose of 600 mg/kg of the compound of Example 1 i.e. the (−)-R,R isomer.

REFERENCE EXAMPLE 1

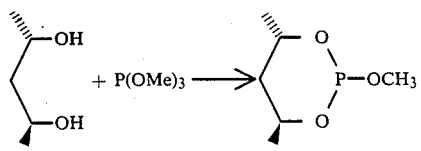

10 g of (+)-(2S,4S)pentane-2,4-diol and 13.6 g of trimethylphosphite were mixed, and heated at 100° C. on an oil bath. After completion of distilling methanol off, the residue is distilled under reduced pressure to obtain colorless transparent 2-methoxy-(4S,6S)-4,6-dimethyl-1,3,2-dioxaphosphorinane. bp: 70°–72° C./15 mmHg.
Yield: 7.5 g
NMR(CDCl$_3$): δ (ppm); 4.8–4.0(2H, m), 3.5(3H, d, J=12 Hz),
2.2–1.5(2H, m), 1.45(3H, d, J=7 Hz),
1.25(3H, d, J=7 Hz)
A similar operation was conducted by using (-)-(2R,4R)pentane-2,4-diol as the starting material, whereby 2-methoxy-(4R,6R)-4,6-dimethyl-1,3,2-dioxaphosphorinane was obtained.

REFERENCE EXAMPLE 2

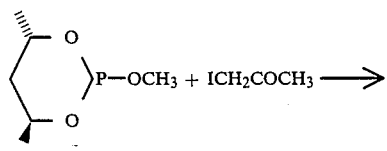

6.2 g of iodoacetone was dissolved in 60 ml of benzene, and the solution was heated on an oil bath at 80° C. A benzene solution (20 ml) of 5.5 g of 2-methoxy-(4S,6S)-4,6-dimethyl-1,3,2-dioxaphosphorinane obtained in Reference Example 1, was dropwise added over a period of 10 minutes. After the completion of the dropwise addition, the mixture was kept at 80° C. for 1 hour, and then the solvent was distilled off under reduced pressure. The residue was subjected to silica gel column chromatography (developer solvent: ethyl acetate/methanol=9/1 (v/v), Rf value: 0.4) to obtain 4.2 g of desired 2-acetonyl-(4S,6S)-4,6-dimethyl-1,3,2-dioxaphosphorinane-2-oxide as a colorless transparent liquid.
NMR(CDCl$_3$): δ (ppm); 5.0–4.5(2H, m), 3.1(2H, d, J=23 Hz),
3.3(3H, s), 1.95(2H), 1.5(3H, dd, J=6.3 Hz, J=0.5 Hz), 1.4(3H, dd, J=6.3 Hz, J=1.5 Hz)
A similar operation was conducted by using 2-methoxy-(4R,6R)-4,6-dimethyl-1,3,2-dioxaphosphorinane as the starting material to obtain 2-acetonyl-(4R,6R)-4,6-dimethyl-1,3,2-dioxaphosphorinane-2-oxide.

REFERENCE EXAMPLE 3

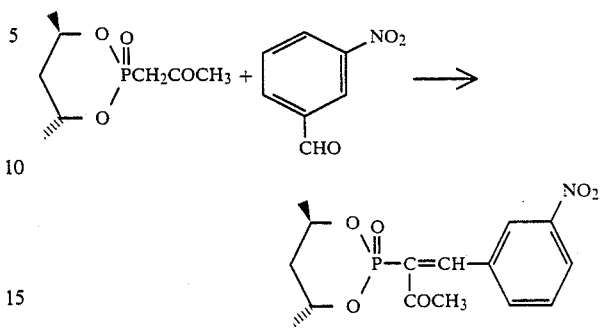

3.38 g of 2-acetonyl-(4R,6R)-4,6-dimethyl-1,3,2-dioxaphosphorinane-2-oxide and 2.4 g of m-nitrobenzaldehyde were dissolved in 15 ml of benzene, and 0.5 ml of piperidine was added thereto. The mixture was refluxed for 5 hours. The reaction solution was subjected to silica gel chromatography (developer solution: ethyl acetate/methanol=9/1 (v/v), Rf value: 0.4) to obtain 1.78 g of desired 2-(1-acetyl-2-(3-nitrophenyl)ethenyl)-(4R,6R)-4,6-dimethyl-1,3,2-dioxaphosphorinane-2-oxide as a yellow viscous liquid.
NMR(CDCl$_3$): δ (ppm); 8.5–7.3(5H, m), 5.2–4.4(2H, m), 2.3(3H, s) 2.0(2H, m), 1.55(3H, d, J=6 Hz), 1.45(3H, d, J=6 Hz)
A similar operation was conducted by using 2-acetonyl-(4S,6S)-4,6-dimethyl-1,3,2-dioxaphosphorinane-2-oxide as the starting material to obtain 2-(1-acetyl-2-(3-nitrophenyl)ethenyl)-(4S,6S)-4,6-dimethyl-1,3,2-dioxaphosphorinane-2-oxide.

EXAMPLE 1

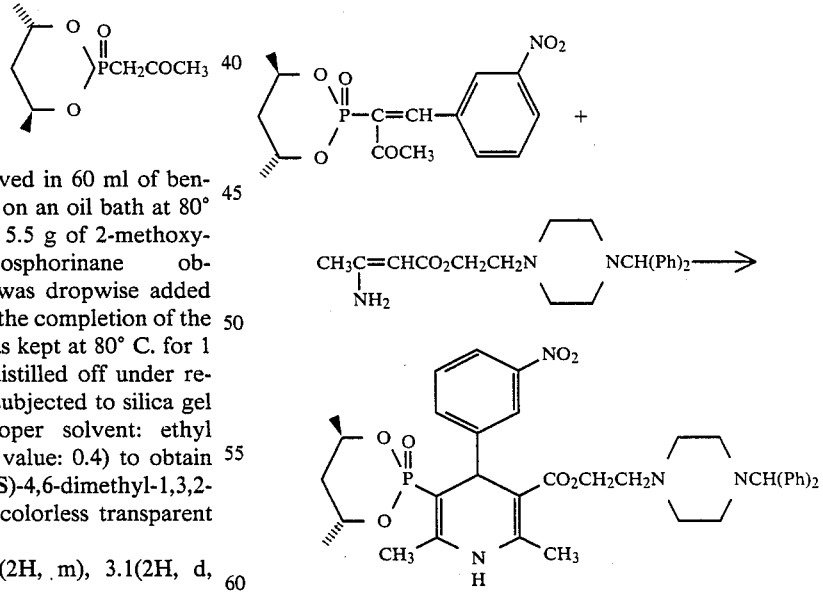

1.7 g of 2-(1-acetyl-2-(3-nitrophenyl)ethenyl)-(4R,6R)-4,6-dimethyl-1,3,2-dioxaphosphorinane-2-oxide and 1.9 g of 3-aminocrotonic acid 4-diphenylmethyl-1-piperadinoethyl ester were dissolved in 10 ml of toluene, and the solution was refluxed for 10 hours. After cooling, the reaction solution was subjected to silica gel chromatography (developer: ethyl acetate/ methanol=9/1 (v/v), Rf value: 0.4) to obtain 2.3 g of desired 5-[(4R,6R)-4,6-dimethyl-1,3,2-dioxaphosphorinan-2-yl]-1,4-dihydro-2,6-dimethyl-4-(3-nitrophenyl)-3-pyridinecarboxylic acid 4-diphenylmethyl-1-piperadinoethyl ester P-oxide, as a yellow liquid.
NMR(CDCl₃): δ (ppm); 8.1–7.1(14H, m), 6.2(1H, broads), 4.9–4.1(6H, m), 2.7–2.2(16H, m), 1.75(2H, m), 1.5–1.0(6H, m)

A similar operation was conducted by using 2-(1-acetyl-2-(3-nitrophenyl)ethenyl)-(4S,6S)-4,6-dimethyl-1,3,2-dioxaphosphorinane-2-oxide as the starting material to obtain 5-[(4S,6S)-4,6-dimethyl-1,3,2-dioxaphosphorinan-2-yl]-1,4-dihydro-2,6-dimethyl-4-(3-nitrophenyl)-3-pyridinecarboxylic acid 4-diphenylmethyl-1-piperadinoethyl ester P-oxide.

Synthesis of a hydrochloride 5.76 g of 5-[(4R,6R)-4,6-dimethyl-1,3,2-dioxaphosphorinan-2-yl]-1,4-dihydro-2,6-dimethyl-4-(3-nitrophenyl)-3-pyridinecarboxylic acid 4-diphenylmethyl-1-piperadinoethyl ester P-oxide was dissolved in 28.8 g of ethanol, and 1.89 g of 35% hydrochloric acid was added. Then, the solvent was distilled off under reduced pressure to obtain a yellow viscous hydrochloride. The angle of rotation of this product was [α]$_D^{25}$: +8.9° C. (c=1.03, MeOH).

Optical resolution

The hydrochloride thus obtained was recrystallized twice with 43 g of ethanol to obtain (−)-5-[(4R,6R)-4,6-dimethyl-1,3,2-dioxaphosphorinan-2-yl]-1,4-dihydro-2,6-dimethyl-4-(3-nitrophenyl)-3-pyridinecarboxylic acid 4-diphenylmethyl-1-piperadinoethyl ester P-oxide dihydrochloride.
Pale yellow crystal, mp: 172°–177°
[α]$_D^{25}$: −16.8° C. (c=0.51, MeOH)

The mother liquors used for the recrystallization were put together, and the solvent was distilled off under reduced pressure, the residue was recrystallized with acetone in an amount of 20 times the weight of the residue. The pale yellow crystal thus obtained was again dissolved in ethanol, and the solvent was distilled off under reduced pressure. The residue was recrystallized with acetone in an amount of 20 times the weight of the residue to obtain (+)-5-[(4R,6R)-4,6-dimethyl-1,3,2-dioxaphosphorinan-2-yl)]-1,4-dihydro-2,6-dimethyl-4-(3-nitrophenyl)-3-pyridinecarboxylic acid 4-diphenylmethyl-1-piperadinoethyl ester P-oxide dihydrochloride.
Pale yellow crystal, mp: 159°–164° C.
[α]$_D^{25}$: +34.8° C. (c=0.51, MeOH)
Free amine NMR(CDCl₃):
NMR values (δ) (ppm) corresponding to various hydrogen atoms were recorded.

(−)-R,R isomer

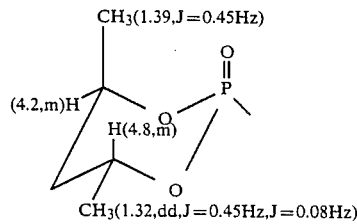

(+)-R,R isomer

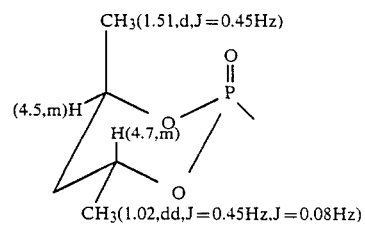

A similar operation was conducted by using 5-[(4S,6S)-4,6-dimethyl-1,3,2-dioxaphosphorinan-2-yl]-1,4-dihydro-2,6-dimethyl-4-(3-nitrophenyl)-3-pyridinecarboxylic acid 4-diphenylmethyl-1-piperadinoethyl P-oxide as the starting material. whereby a (+)-S,S isomer precipitated from the ethanol solution, and a (−)-S,S isomer precipitated from the acetone solution. The (+)-S,S isomer was recrystallized from ethanol for purification. Likewise, the (−)-S,S isomer was dissolved in ethanol, and after distilling off the solvent and an addition of acetone, recrystallized from acetone for purification.

(+)-S,S isomer
Pale yellow crystal, mp: 172°–177° C.
[α]$_D^{25}$: +16.9° C. (c=0.52, MeOH)
(−)-S,S isomer
Pale yellow crystal, mp: 159°–164° C.
[α]$_D^{25}$: −34.8° C. (c=0.51, MeOH)

The NMR spectrum of free amine in the case of the (+)-S,S isomer exactly corresponded to the spectrum of the (−)-R,R isomer. Likewise, the NMR spectrum of free amine in the case of the (−)-S,S isomer exactly corresponded to the spectrum of the (+)-R,R isomer.

FORMULATION EXAMPLE 1: Tablets

Composition (1,000 tablets)

| | |
|---|---|
| Hydrochloride of the (−)-R,R isomer of Example 1 | 5.0 (g) |
| Lactose | 190.0 |
| Corn starch | 75.0 |
| Crystal cellulose powder | 25.0 |
| Methyl cellulose | 3.0 |
| Magnesium stearate | 2.0 |
| | 300.0 |

The above ingredients in the respective amounts were introduced into a twin shell mixer and uniformly mixed. This powder mixture was tableted by a direct compression method to obtain tablets having a weight of 300 mg per tablet.

FORMULATION EXAMPLE 2: Capsules

Composition (1,000 tablets)

| | |
|---|---|
| Hydrochloride of the (−)-R,R isomer of Example 1 | 5.0 (g) |
| Corn starch | 145.0 |
| Crystal cellulose powder | 145.0 |
| Magnesium stearate | 5.0 |
| | 300.0 |

The above ingredients in the respective amounts were introduced into a twin shell mixer and uniformly mixed. This powder mixture was packed in hard gelatin capsules in an amount of 300 mg per capsule.

FORMULATION EXAMPLE 3: Syrups

Composition (2% syrups)

| | |
|---|---|
| Hydrochloride of the (−)-R,R isomer of Example 1 | 2.0 (g) |
| Sugar | 30.0 |
| Glycerin | 5.0 |
| Flavoring agent | 0.1 |
| 96% ethanol | 10.0 |
| Methyl p-hydroxybenzoate | 0.03 |
| Distilled water | Add to bring the total amount to 100.0 g |

The sugar and the hydrochloride of the compound of Example were dissolved in 60 g of warm water, and after cooling the solution, a solution of the flavoring agent in glycerin and ethanol was added. Then, water was added to this mixture to bring the total amount to 100.0 g.

FORMULATION EXAMPLE 4: powder

Composition

| | |
|---|---|
| Hydrochloride of the (−)-R,R isomer of Example 1 | 1.0 (g) |
| Lactose | 88.0 |
| Crystal cellulose powder | 10.0 |
| Methyl cellulose | 1.0 |
| | 100.0 |

The above ingredients in the respective amounts were introduced into a twin shell mixer and uniformly mixed to obtain a powder.

What is claimed is:

1. An optical isomer of a compound having the formula:

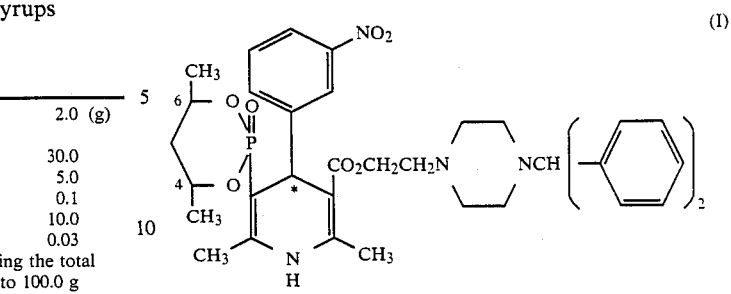

wherein the two methyl groups at 4- and 6-positions of the dioxaphosphorinane ring assume trans configurations to each other, which has a levo-rotatory angle of optical rotation attributable to the asymmetric carbon atom at 4-position of the dihydropyridine ring, and a pharmaceutically acceptable salt thereof.

2. The optical isomer according to claim 1, which is a levo-rotatory optical isomer of a compound having the formula:

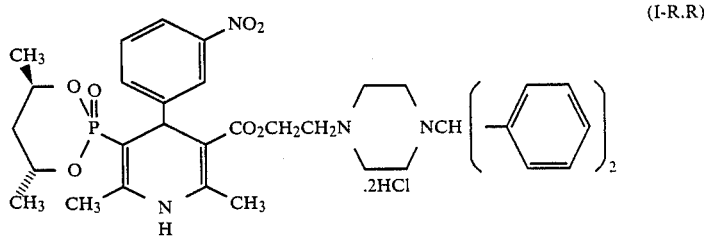

wherein the two methyl groups at 4- and 6-positions of the dioxaphosphorinane ring assume (R,R) configurations.

3. The optical isomer according to claim 1, which is a levo-rotatory optical isomer of a compound having the formula:

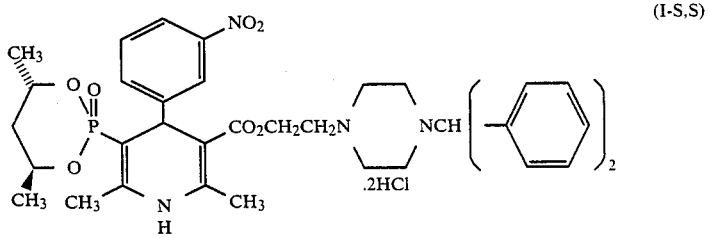

wherein the two methyl groups at 4- and 6-positions of the dioxaphosphorinane ring assume (S,S) configurations.

4. A vasodilator composition comprising an effective amount of an optical isomer as defined in claim 1 or its pharmaceutically acceptable salt, and a pharmaceutically acceptable diluent or carrier.

5. A method for treating a disease of a circulatory organ of a mammal selected from the group consisting of angina pectoris, disturbance of cerebral circulation or hypertension, which comprises administering an effective amount of an optical isomer as defined in claim 1 and its pharmaceutically acceptable salt to the mammal.

* * * * *